(12) United States Patent
Ashihara et al.

(10) Patent No.: US 7,220,231 B2
(45) Date of Patent: May 22, 2007

(54) WALKING CONDITION DETERMINING DEVICE AND METHOD

(75) Inventors: Jun Ashihara, Wako (JP); Hisashi Katoh, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 297 days.

(21) Appl. No.: 10/491,853

(22) PCT Filed: Aug. 23, 2002

(86) PCT No.: PCT/JP02/08528

§ 371 (c)(1),
(2), (4) Date: Apr. 7, 2004

(87) PCT Pub. No.: WO03/032832

PCT Pub. Date: Apr. 24, 2003

(65) Prior Publication Data

US 2004/0249316 A1 Dec. 9, 2004

(30) Foreign Application Priority Data

Oct. 18, 2001 (JP) ............................. 2001-320430

(51) Int. Cl.
*A61B 5/103* (2006.01)
*A61B 5/117* (2006.01)

(52) U.S. Cl. .................... 600/595; 600/587; 600/592

(58) Field of Classification Search ................ 600/587, 600/592, 595
See application file for complete search history.

(56) References Cited

U.S. PATENT DOCUMENTS 4,631,676 A * 12/1986 Pugh .......................... 600/595

(Continued)

FOREIGN PATENT DOCUMENTS

| JP | 07-163607 | 6/1995 |
|---|---|---|
| JP | 11-347020 | 12/1999 |
| JP | 2000-325329 | 11/2000 |
| JP | 2001-108479 | 4/2001 |

OTHER PUBLICATIONS

Sachiko Hisashita et al., "Nichijo Seikatsu ni okeru Jokashi Undo no Keisoku", Human Interface, Feb. 16, 1999, vol. 1, No. 1, pp. 53 to 56.

(Continued)

*Primary Examiner*—Max F. Hindenburg
*Assistant Examiner*—Anuradha Roy
(74) *Attorney, Agent, or Firm*—Rankin, Hill, Porter & Clark LLP

(57) ABSTRACT

A device and a method that permit easy and accurate determination of a walking condition regardless of differences in foot landing points on soles or lengths of legs of a walker are provided. According to this device, a measuring device measures a parameter indicating a displacement amount of a bottom end portion of a leg of the walker. A first storage device stores patterns of plots in a determination space corresponding to parameters and walking conditions of the walker such that they are associated with each other. Furthermore, a generating device generates plots defined in the determination space by parameters measured by the measuring device. Then, a determining device determines walking conditions of the walker on the basis of the patterns of the plots stored in conjunction with the walking conditions by the first storage device and the patterns of the plots generated by the generating device.

4 Claims, 5 Drawing Sheets

U.S. PATENT DOCUMENTS 4,813,436 A * 3/1989 Au ............................. 600/592
5,957,870 A * 9/1999 Yamato et al. .............. 600/592
6,165,143 A * 12/2000 van Lummel ............... 600/595

OTHER PUBLICATIONS

Goro Nebuya et al., "Kado Sokudo oyobi Kasokudo Censer o Shiyo shita . . . ", BPES2000, Oct. 13, 2000, pp. 233 to 236.

* cited by examiner

WALKING CONDITION DETERMINING DEVICE AND METHOD

BACKGROUND OF THE INVENTION

1. Technical Field

The present invention relates to a device and a method for determining a walking condition of a walker having a plurality of legs.

2. Description of Related Art

When a device for aiding a person with deteriorated muscle strength in walking is used, it is necessary to accurately determine a walking condition, that is, whether the person is walking on a level ground, walking up or down stairs, etc. in order to properly aid the walking by the device. For this purpose, Japanese Laid-Open Patent No. 7-163607, for example, has proposed a method for determining a walking condition on the basis of pressures applied to soles of a walker measured by pressure sensors. Furthermore, Japanese Laid-Open Patent No. 2000-325329, for example, has proposed a method for determining a walking condition on the basis of angles of legs of a walker.

However, according to the determining method based on the pressures applied to soles, portions of the soles where the pressure sensors are provided may not touch stair steps especially when a walker is going up or down stairs, and walking conditions may be erroneously determined. For instance, there are cases where the walker lands on a stair at his or her tiptoes, whereas the pressure sensors are provided at their heels. Furthermore, distribution of pressures applied to soles varies, depending upon the shapes of soles of footwear, so that walking conditions may also be erroneously determined. If footwear having pressures sensors provided in its soles is used, then the pressure sensors and an arithmetic processing unit or the like for determining walking conditions must be connected or disconnected through communication lines or electric wires each time the footwear is attached or detached. This may cause the walker to feel bothersome.

According to the determining method based on the angles of legs, walking conditions may not be accurately determined, depending on lengths of the legs of a walker. For instance, when walkers climb the same stairs, the extent to which their thighs are raised for walking differs according to the length of their legs. As a result, it may be erroneously determined that a walker is climbing stairs if the walker is short, while it may be erroneously determined that the walker is walking on a level ground if the walker is tall.

Especially in the walk aiding device, erroneous determination of walking conditions leads to excessive or inadequate aiding power imparted to a walker, adversely affecting the walking.

Accordingly, the present invention has been made with a view toward solving the problems described above by providing a device and a method that allow walking conditions to be determined easily and accurately, regardless of differences in landing spots on soles or in length of legs of walkers.

BRIEF SUMMARY OF THE INVENTION

A walking condition determining device in accordance with the present invention for solving the problems described above is characterized by being equipped with a measuring means for measuring a parameter that indicates a displacement amount of a bottom end portion of a leg of the aforesaid walker, a first storage means for storing a pattern of a plot in a determination space that corresponds to the parameter and a walking condition of the walker such that they are associated with each other, a generating means for generating a plot defined in the determination space by the parameter measured by the measuring means, and a determining means for determining a walking condition of the walker on the basis of comparison between a pattern of a plot stored in association with walking conditions by the first storage means and a pattern of the plot generated by the generating means.

A walking condition determining method in accordance with the present invention for solving the problems described above is characterized by including a measuring step for measuring a parameter that indicates a displacement amount of a bottom end portion of a leg of the walker, an associating step for associating a pattern of a plot in a determination space corresponding to the parameter with a walking condition of the walker, a generating step for generating a plot defined in the determination space by the parameter measured in the measuring step, and a determining step for determining a walking condition of the walker on the basis of comparison between patterns of plots associated with walking conditions in the associating step and the pattern of the plot generated in the generating step.

The displacement amount of a bottom end portion of a leg that is measured in the present invention depends heavily on a walking place, e.g., a level ground or stairs, and hardly depends on differences in landing spots on soles or the length of legs of a walker. For this reason, a pattern of a plot in a determination space defined by a parameter indicating the displacement amount remains substantially the same under the same walking condition, independently of the differences in landing spots on soles or the length of legs of a walker. In addition, the present invention does not involve bothersome connection or disconnection of wiring required each time special footwear for pressure measurement is attached or detached. Thus, the present invention makes it possible to easily and accurately determine a walking condition on the basis of a plot pattern in a determination space regardless of differences in landing spots on soles or length of legs of a walker.

The first storage means stores a plot configuration pattern in the determination space as the plot pattern. The determining means determines a walking condition of the walker on the basis of the determination whether the configuration pattern stored in by the first storage means is identical or similar to a generated plot configuration pattern generated by the generating means.

According to the present invention, a walking condition can be determined on the basis of a "configuration pattern," that is, a pattern of a plotted configuration drawn in the determination space.

Furthermore, the first storage means stores an existence plot pattern in the determination space as the plot pattern, and the determining means determines a walking condition of the walker on the basis of whether the existence pattern stored by the first storage means is identical or similar to an existence plot pattern generated by the generating means.

According to the present invention, it is possible to determine a walking condition on the basis of an "existence pattern" showing regions in the determination space wherein plots exist.

The measuring means is provided with a first measuring means for measuring, as a first parameter, a difference between the length of a leg of the walker and a vertical interval between a top end portion and a bottom end portion of the leg. The determining means determines that the walker is in a normal walking condition if an existence pattern indicates that a plot in the determination space is located in a low region wherein the first parameter is below a predetermined threshold value, whereas it determines that the walker is in a slope walking condition if an existence pattern indicates that a plot is located in a high region wherein the first parameter is the predetermined threshold value or more.

Furthermore, the measuring means is equipped with a second measuring means for measuring, as a second parameter, a longitudinal position of a bottom end portion of a leg with respect to a top end portion of the leg of the walker. When the determining means determines that the walker is in the slope walking condition, the determining means determines that the walker is in an ascending walking condition if the plot in the determination space indicates an existence pattern in which the plot is in a predetermined positive region wherein the second parameter takes a positive threshold value or more, whereas the determining means determines that the walker is in a descending walking condition if the plot in the determination space indicates an existence pattern in which the plot is in a predetermined negative region wherein the second parameter takes a negative threshold value or less.

According to the present invention, although details will be discussed hereinafter, walking conditions can be accurately determined on the basis of qualitative speculation of displacement amounts of leg bottom end portions that are represented by the first and second parameters and reflected on plot existence patterns in the determination space.

The "normal walking condition" means a condition in which a walker is walking on a level ground, a gentle slope, or a stairs with small step height differences. The "slope walking condition" means a condition in which a walker is walking a steep slope or stairs with large step height differences. Here, whether a sloping road is gentle or steep, or whether stairs have small or large step height differences is determined by setting the "predetermined absolute value."

The present invention is characterized by being equipped with a second storage means for storing joint-to-joint distances of the legs of the walker and an angle sensor for measuring joint angles of the legs, and a first and a second measuring means measure first and second parameters on the basis of the joint-to-joint distances stored by the second storage means and joint angles measured by the angle sensor.

The present invention makes it possible to measure joint-to-joint distances of the legs and joint angles and the first and second parameters on the basis of a simple geometric speculation, as will be discussed hereinafter.

The determining means determines a walking condition of the walker on the basis of a series of plots generated by the generating means over an immediately preceding walking period of the walker.

Furthermore, the present invention is characterized by being equipped with an acceleration sensor for measuring vertical acceleration of an upper portion of a leg of the walker and a walking period measuring means for measuring a walking period of the walker on the basis of the vertical acceleration measured by the acceleration sensor.

According to the present invention, a walking condition of a walker can be determined on the basis of a plot pattern drawn for each walking period in a determination space.

DETAILED DESCRIPTION OF THE INVENTION

Figure 1:
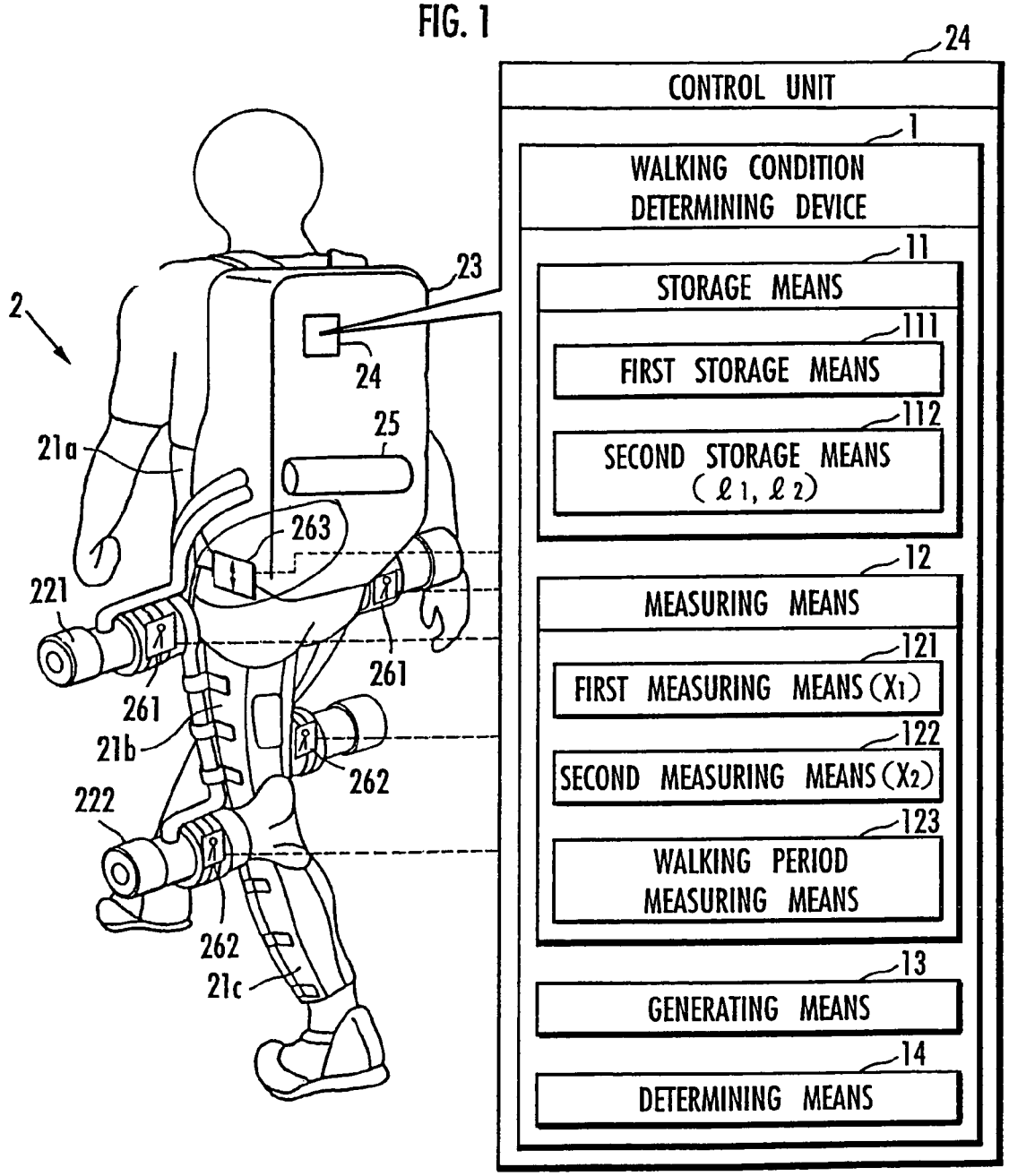
FIG. 1 is a construction explanatory diagram of a walking condition determining device according to the present embodiment.

A walking condition determining device and method in accordance with the present invention will be explained in conjunction with accompanying drawings. A walking condition determining device 1 shown in FIG. 1 constitutes a part of a walk aiding apparatus 2 used by being attached to a human being, who is a walker.

The walk aiding apparatus 2 is provided with supporters 21a, 21b, and 21c attached to the abdomen, thighs, and shins of the walker, a first actuator 221 located at the waist of the walker to impart torque about hip joints through the intermediary of the supporters 21a and 21b, a second actuator 222 located at knees of the walker to impart torque about knee joints through the intermediary of the supporters 21b and 21c, a control unit 24 accommodated in a backpack 23 on the back of the walker to control operations or the like of the actuators 221 and 222, and a battery 25 also accommodated in the backpack 23 to supply power to the actuators 221 and 222.

The walk aiding apparatus 2 is further provided with first angle sensors 261 located on the waist of the walker to measure a hip joint angle $\theta_1$, second angle sensors 262 located on the knees of the walker to measure a knee joint angle $\theta_2$, and a G sensor (acceleration sensor) 263 located on the waist of the walker to measure vertical acceleration.

Figure 3:
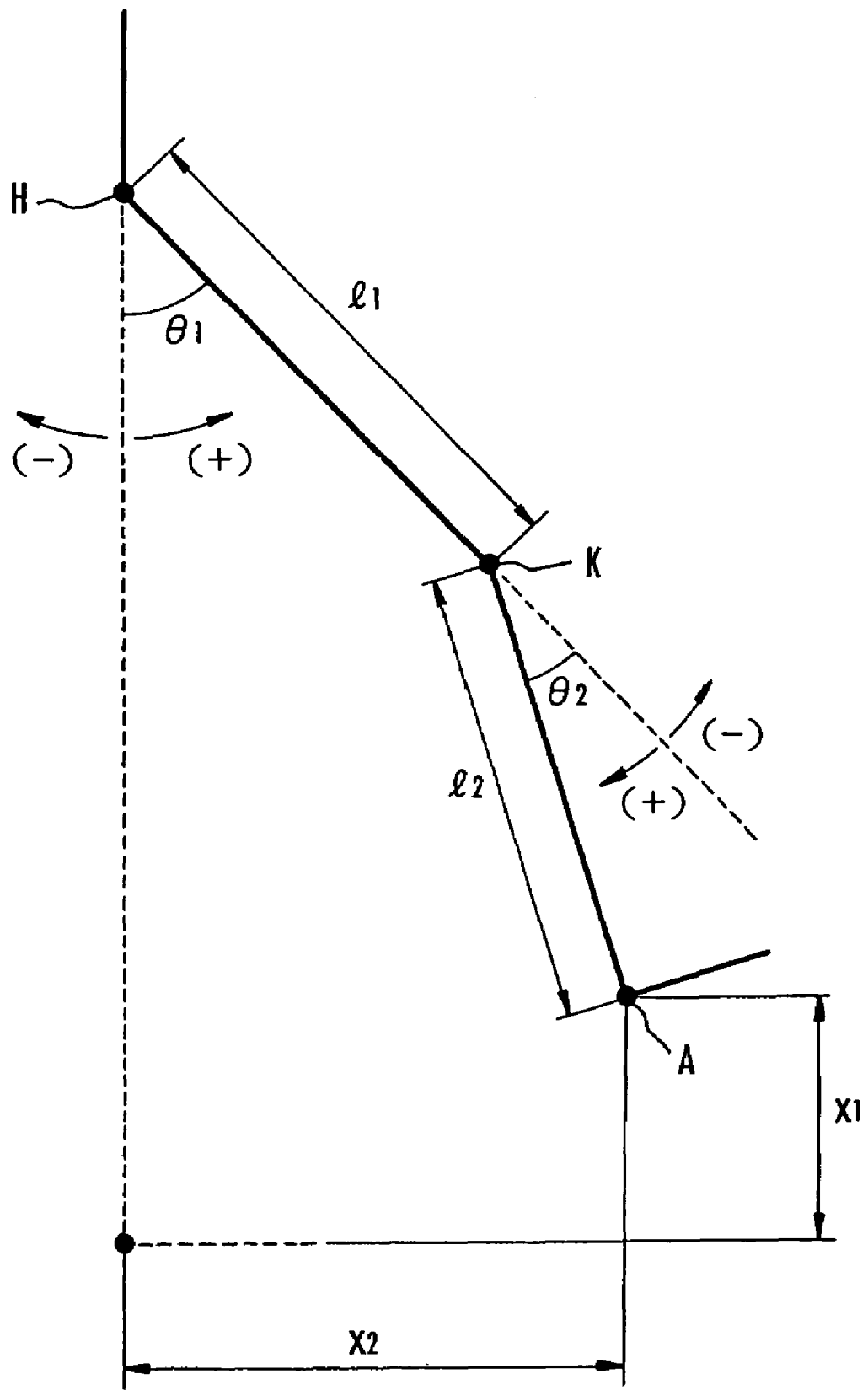
FIG. 3 is an explanatory diagram of a method of measuring first and second parameters according to the present embodiment.

According to a leg model shown in FIG. 3, the hip joint angle $\theta_1$ is an angle formed by a thigh having a length $l_1$ with respect to a vertical plane that includes a hip joint H. The angles are defined as positive angles if the thighs are ahead of the plane, while they are defined as negative if the thighs are behind the plane. The knee joint angle $\theta_2$ is an angle formed by a shin having a length $l_2$ with respect to a plane that includes a thigh. The angles are defined as negative angles if the shins are ahead of the plane, while they are defined as positive if the shins are behind the plane.

The walking condition determining device 1 is equipped with a storage means 11, a measuring means 12, a generating means 13, and a determining means 14 that partly constitute the control unit 24.

The storage means 11 constructed of a ROM, a RAM, and the like is equipped with a first storage means 111 for storing plot existence patterns (refer to FIG. 4) in the determination space and walking conditions of the walker such that they are associated with each other, and a second storage means 112 for storing a distance $l_1$ between a hip joint and a knee joint of the walker and a distance $l_2$ between a knee joint and a foot joint of the walker, the distances being measured in advance.

The measuring means 12 is provided with a first measuring means 121, a second measuring means 122, and a walking period measuring means 123.

The first measuring means 121 includes, as components, a first angle sensor 261, a second angle sensor 262, and a second storage means 112. Based on the hip joint angle $\theta_1$ and the knee joint angle $\theta_2$ of the walker measured by the first and second sensors 261 and 262, and the joint-to-joint distances $l_1$ and $l_2$ stored in the second storage means 112, the first measuring means 121 measures a difference between the length of a leg from a hip joint to a foot joint of the walker $l_1+l_2$ and a vertical interval between the hip joint and the foot joint (first parameter: refer to FIG. 3) $x_1$.

Similarly, the second measuring means 122 includes, as components, a first angle sensor 261, a second angle sensor 262, and a second storage means 112. Based on the hip joint angle $\theta_1$ and the knee joint angle $\theta_2$ of the walker measured by the first and second sensors 261 and 262, and the joint-to-joint distances $l_1$ and $l_2$ stored in the second storage means 112, the second measuring means 122 measures a longitudinal position (second parameter: refer to FIG. 3) $x_2$ of the foot joint (bottom end portion of a leg) in relation to the hip joint (top end portion of the leg) of the walker.

The walking period measuring means 123 includes a G sensor 263 as a component, and measures a walking period of the walker on the basis of changes in vertical acceleration that take place at the waist of the walker measured by the G sensor 263.

The generating means 13 constructed of a CPU, a signal input/output circuit, a RAM, a ROM, etc. generates "plots (plotting data)", which will be discussed hereinafter, in a two-dimensional "determination space" associated with the first parameter $x_1$ and the second parameter $x_2$.

Similarly, the determining means 14 constructed of a CPU, a signal input/output circuit, the first storage means 111, etc. determines the walking condition of the walker on the basis of a plot existence pattern generated by the generating means 13 and a plot existence pattern stored by the first storage means 111, as will be discussed hereinafter.

Functions of a walking condition determining device 1 will now be explained in conjunction with FIG. 2 to FIG. 5.

Figure 2:
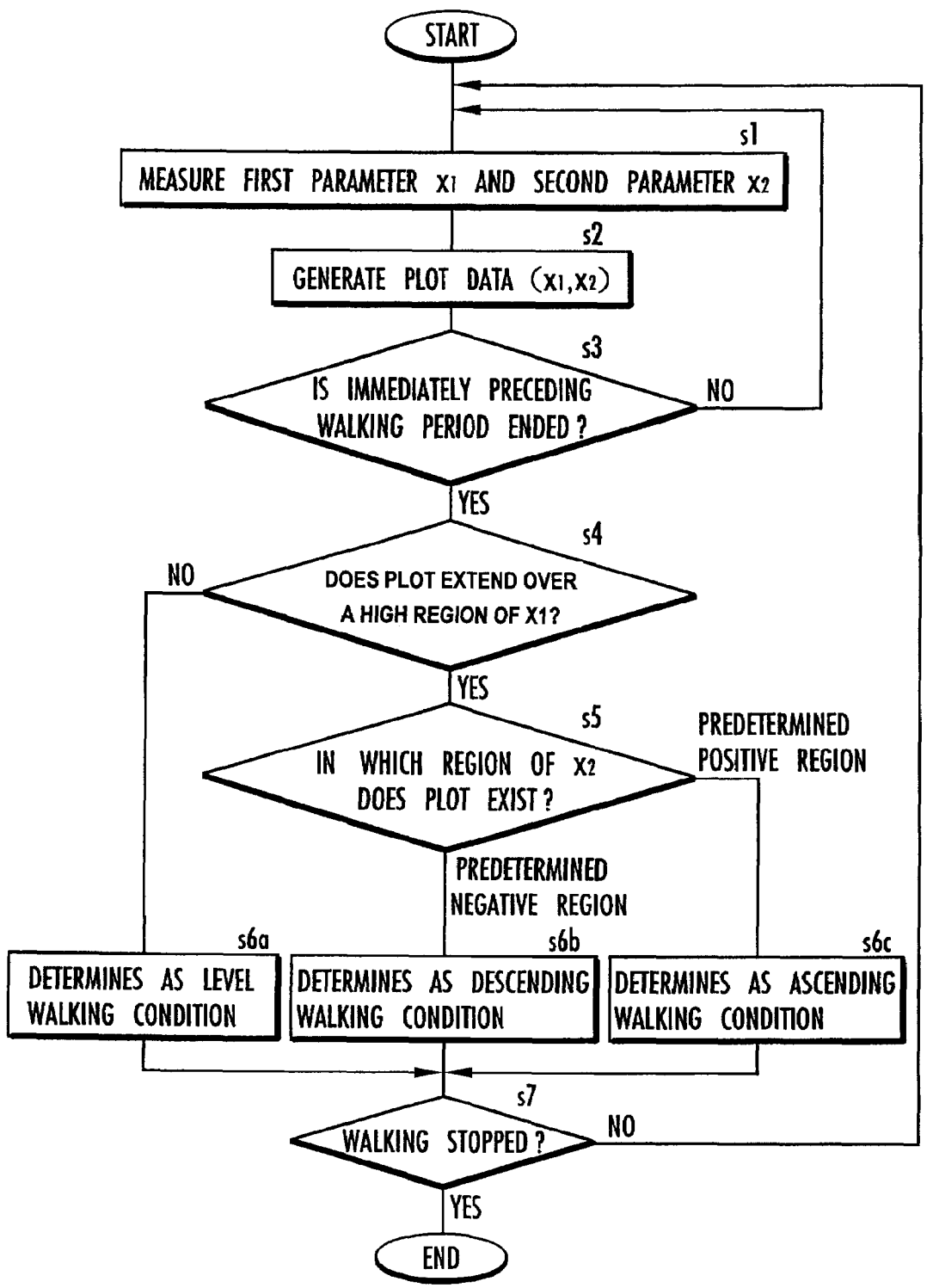
FIG. 2 is an explanatory diagram showing a procedure of a walking condition determining method according to the present embodiment.

First, the first and second measuring means 121 and 122 measure the first and second parameters $x_1$ and $x_2$ (s1 shown in FIG. 2). The measurement is performed according to expressions (1) and (2) below, using the hip-to-knee and knee-to-foot joint distances $l_1$ and $l_2$ of the walker stored by the second storage means 112, and the hip and knee joint angles $\theta_1$ and $\theta_2$ measured by the first and second angle sensors 261 and 262.

$$X_1 = l_1 + l_2 - \{l_1 \cos \theta_1 + l_2 \cos(\theta_1 - \theta_2)\} \quad (1)$$

$$X_2 = l_1 \sin \theta_1 + l_2 \sin(\theta_1 - \theta_2). \quad (2)$$

Expressions (1) and (2) are based on simple geometric speculation in the leg model shown in FIG. 3. The first parameter $x_1$ indicates an amount of variation in the vertical interval of a foot joint A with respect to a hip joint H in comparison with an upright state in which joints H, K and A are on a vertical line (dashed line in FIG. 3). The second parameter $x_2$ indicates an amount of variation in the longitudinal direction of the foot joint A with respect to the hip joint H in comparison with an upright state (dashed line in FIG. 3).

Next, the generating means 13 generates a "plot" defined by the first and second parameters ($x_1$, $x_2$) measured by the first and second measuring means 121 and 122 in the two-dimensional "determination space" (s2 in FIG. 2).

The walking period measuring means 123 determines whether the immediately preceding walking period has ended on the basis of a change in vertical acceleration that takes place at waist measured by the G sensor 263 (s3 in FIG. 2). To be more specific, it is determined that an immediately preceding walking period has ended each time the vertical acceleration significantly increases twice when one leg lands on a floor and then the other leg lands in comparison with the vertical acceleration when legs leave the floor. Until the determination is made (NO in s3 in FIG. 2), the measurement of the first and second parameters $x_1$ and $x_2$ (s1 in FIG. 2) and the generation of a plot (s2 in FIG. 2) are repeated. A track on a plot ($x_1$, $x_2$) drawn in one walking period is represented by the curves shown in FIG. 5(a) to FIG. 5(c).

If it is determined that the immediately preceding walking period is finished (YES in s3 in FIG. 2), then the determining means 14 determines a walking condition. For this determination, the existence patterns stored in association with walking conditions by the first storage means 111, that is, the patterns indicating the regions in the determination space wherein plots exist are used (refer to FIG. 4). According to the association relationship, the determination space is divided into a "low region" wherein the first parameter $x_1$ takes a value below a predetermined threshold value $c_+$ (>0) and a "high region" wherein it takes a value of the predetermined threshold value c or more. The determination space includes a "predetermined positive region" wherein the second parameter $x_2$ takes a positive threshold value $c_+$ (>0) or more and a "predetermined negative region" wherein it takes a negative threshold value $c_-$ (<0) or less. A pattern in which a plot exists only in the low region $\{x_1<c\}$ is associated with the "normal walking condition," a pattern in which a plot exists only in an overlapping region of the high region and a predetermined negative region $\{x_1 \geq c, x_2 \leq c_-\}$ is associated with the "descending walking condition," and a pattern in which a plot exists in an overlapping region of the high region and a predetermined positive region $\{x_1 \geq c, x_2 \geq c_+\}$ is associated with the "ascending walking condition."

To determine a walking condition, it is first determined whether a plot ($x_1$, $x_2$) exists in the high region $\{x_1 \geq c\}$ of the determination space (s4 in FIG. 2). If the plot pattern is determined to be the existence pattern in which no part of the plot ($x_1$, $x_2$) exists in the high region $\{x_1 \geq c\}$ and the entire plot exists in the low region $\{x_1<c\}$ (NO in s4 in FIG. 2), as shown in FIG. 5(a), then it is determined that the walker is in the "normal walking condition" (s6a in FIG. 2).

Conversely, if it is determined that the existence pattern indicates the presence of a plot in the high region $\{x_1 \geq c\}$ (YES in s4 in FIG. 2), then it is further determined whether at least a part of the plot in the high region $\{x_1 \geq c\}$ is in the predetermined negative region $\{x_2 \leq c\}$ or the predetermined positive region $\{x_2 \geq c_+\}$ (s5 in FIG. 2). If the pattern is determined to be the existence pattern in which the plot is in the predetermined negative region $\{x_2 \leq c_-\}$, then it is determined that the walker is in the "descending walking condition" (s6b in FIG. 2). If the pattern is determined to be the existence pattern in which the plot is in the predetermined positive region $\{x_2 \geq c_+\}$, then it is determined that the walker is in the "ascending walking condition" (s6c in FIG. 2).

The walking condition is determined for each walking period (s1 to s6 in FIG. 2) unless the walker stops walking (NO in s7 in FIG. 2). Then, based on a determined walking condition, the control unit 24 decides torque to be applied to the legs, and the torque is applied through the intermediary of the first and second actuators 221 and 222.

As described above, the first parameter $x_1$ represents the amount of variation in the vertical interval of the foot joint (the bottom end portion of a leg) A with respect to the hip joint (the top end portion of the leg) H on the basis of the upright state (dashed line) in which the joints H, K, and A are on the straight line in FIG. 3. The second parameter $x_2$ represents the amount of variation in the longitudinal direction of the foot joint (the bottom end portion of a leg) A with respect to the hip joint (the top end portion of the leg) H on the basis of the upright state. The amounts of variation mainly depend on the landing positions of the walker's legs and hardly depend on differences of landing points in soles or leg length of the walker.

To be more specific, the existence of a plot in the high region $\{x_1 \geq c\}$ of the determination space (refer to s4 in FIG. 2) depends on whether the leg bottom end portions are significantly displaced or not for walking on stairs or the like, and hardly depends on differences of landing points in soles or length of legs. Furthermore, the existence of a plot in an overlapping region of the high region $\{x_1 \geq c\}$ and the predetermined negative region $\{x_2 \leq c_-\}$ or the predetermined positive region $\{x_2 \geq c_+\}$ depends on whether the leg bottom end portions are at front or back when the leg bottom end portions are significantly displaced to walk up or down stairs or the like, and hardly depends on differences of landing points in soles or length of legs.

Figure 5:
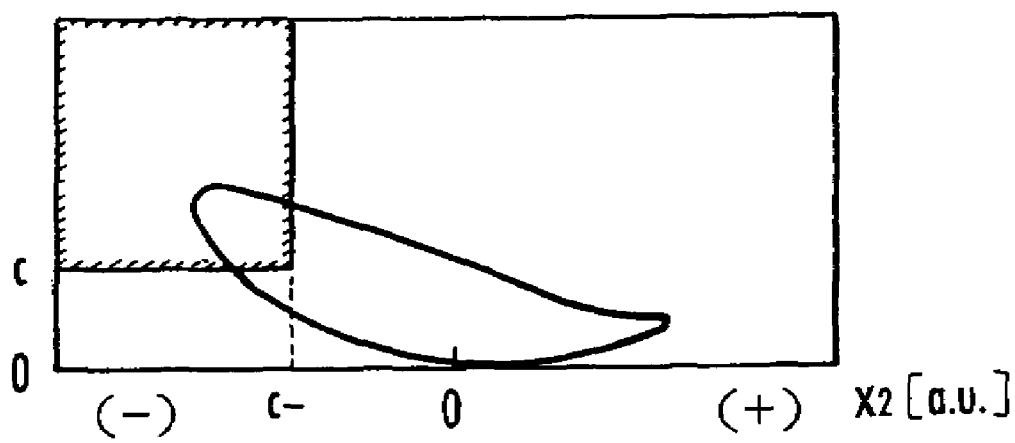
FIG. 5 is an explanatory diagram of walking condition determination results in the present embodiment.
Figure 5:
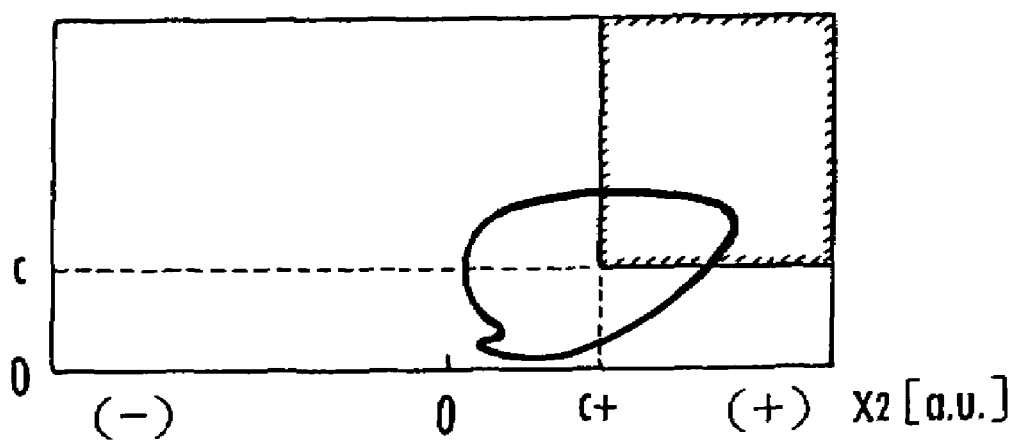
Figure 5:
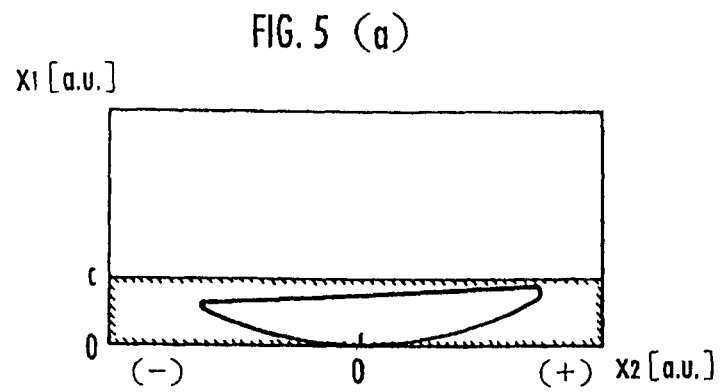
Figure 5:
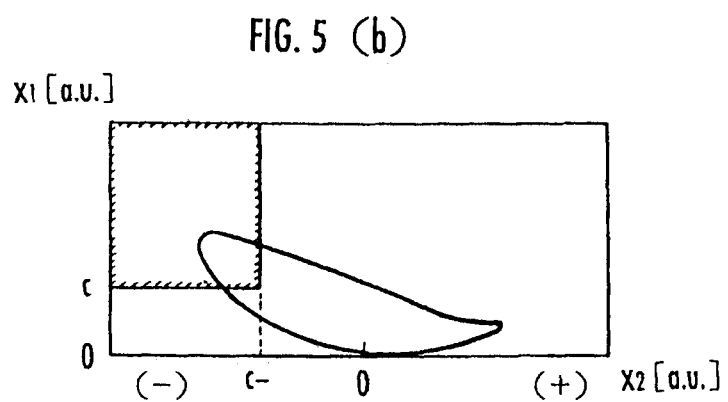
Figure 5:
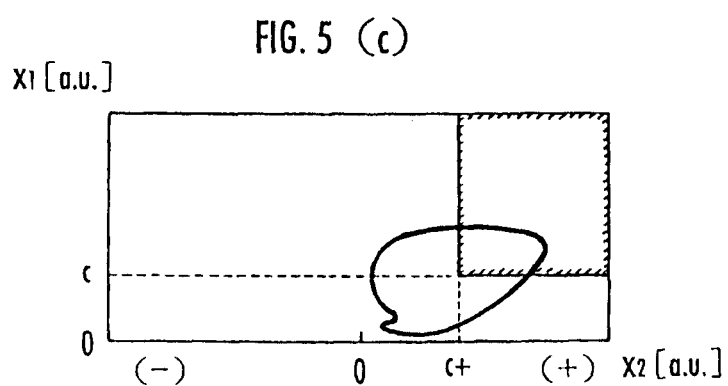

Thus, according to the device 1, plot existence patterns defined by the first and second parameters $x_1$ and $x_2$ will be substantially the same in the determination space when the walking condition is the same, irrespectively of differences of landing points in soles or length of legs of a walker (refer to FIG. 5(*a*) to FIG. 5(*c*)). Moreover, the device 1 involves no special footwear that includes pressure sensors for determining walking conditions and has to be attached and detached, which requires connection and disconnection of various types of wires. Hence, walking conditions can be determined easily and accurately on the basis of plots ($x_1$, $x_2$) in the determination space regardless of differences in landing spots in the soles of walkers or differences in the length of legs.

In the present embodiment, the walker is a human being. However, in other embodiments, the walkers may be various types of two- or four-legged walking animals, humanoid robots or zoomorphic robots.

In the present embodiment, the two parameters $x_1$ and $x_2$ have been measured as the parameters representing a positional relationship of foot joints with respect to hip joints, and walking conditions have been determined on the basis of the plots in the two-dimensional determination space. As another embodiment, one parameter (e.g., $x_1/x_2$) may be measured as the aforesaid parameter, and a walking condition may be determined on the basis of a plot in a one-dimensional determination space. Alternatively, three or more parameters (e.g., $x_1$ and $x_2$ of all legs) may be measured, and a walking condition may be determined on the basis of plots in a determination space of three or more dimensions.

In the present embodiment, walking conditions have been determined on the basis of the existence patterns showing in which regions of the determination space plots exist. As an alternative embodiment, walking conditions may be determined on the basis of a configuration pattern of plot drawn in the determination space over a predetermined period, such as one walking period.

Figure 4:
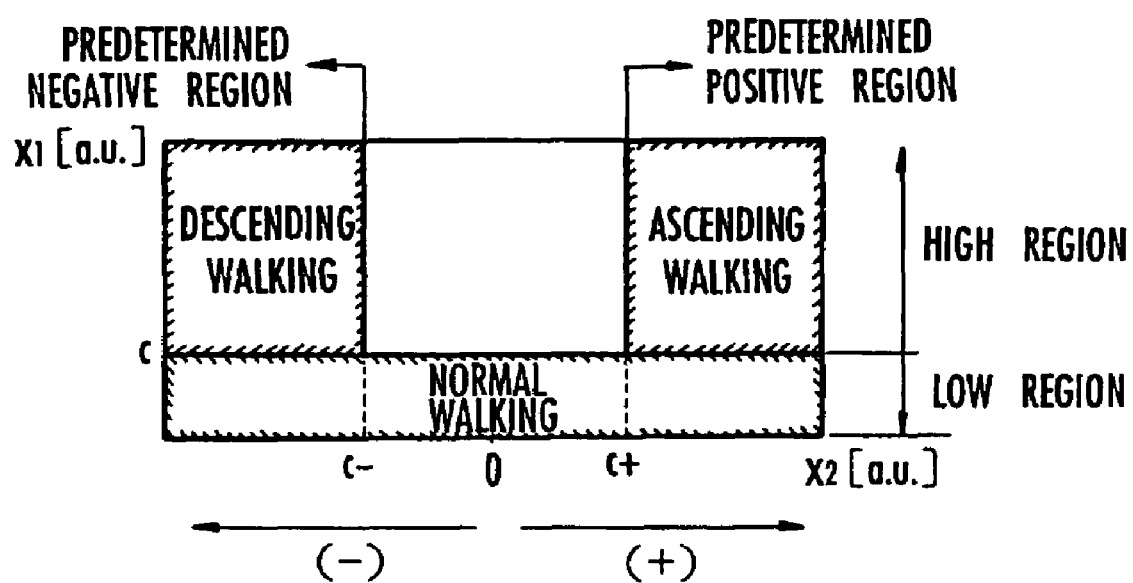
FIG. 4 is an explanatory diagram of an association relationship between the determination space and walking conditions in the present embodiment.

In the present embodiment, three different walking conditions associated with the three regions in the determination space have been determined (refer to s6*a* to 6*c* in FIG. 2, and FIG. 4). As another embodiment, the determination space may be divided into more regions, so that more walking conditions may be determined on the basis of the more regions. For instance, more detailed walking conditions can be determined if steepness of hills or difference in step height of stairs is divided into more steps. This allows the control unit 24 of the walk aiding apparatus 2 to properly determine torque to be imparted to a walker on the basis of determination of more detailed walking conditions.

In the present embodiment, the walking conditions have been determined each time one walking period elapses (refer to s3 in FIG. 2). As another embodiment, however, walking conditions may be steadily determined. For example, it may be determined that a walker is in the "ascending walking condition" immediately after it is determined that a plot ($x_1$, $x_2$) is in a region $\{x_1 \geq c, x_2 \geq c_+\}$ of a determination space, or it may be determined that the walker is in the "descending walking condition" immediately after it is determined that the plot is in a region $\{x_1 \geq c, x_2 \leq c_-\}$.

The invention claimed is:

1. A walking condition determining device for determining a walking condition of a walker having a plurality of legs, comprising:
    a measuring means for measuring a parameter that indicates a displacement amount of a bottom end portion of a leg of the walker;
    a first storage means for storing a pattern of a plot in a determination space corresponding to the parameter and a walking condition of the walker such that they are associated with each other;
    a generating means for generating a plot defined in the determination space by the parameter measured by the measuring means; and
    a determining means for determining the walking condition of the walker on the basis of comparison between the pattern of the plot stored in association with the walking condition by the first storage means and a pattern of the plot generated by the generating means,
    wherein the first storage means stores an existence pattern of a plot in the determination space as the plot pattern, and the determining means determines the walking condition of the walker on the basis of the determination whether or not the existence pattern stored by the first storage means is identical or similar to an existence pattern of the plot generated by the generating means,
    wherein the measuring means comprises a first measuring means for measuring, as a first parameter, a difference between the length of a leg of the walker and a vertical interval between a top end portion and a bottom end portion of the leg, and
    the determining means determines that the walker is in a normal walking condition if an existence pattern indicates that a plot in the determination space is located in a low region wherein the first parameter is below a predetermined threshold value, whereas it determines that the walker is in a slope walking condition if an existence pattern indicates that a plot is located in a high region wherein the first parameter is the predetermined threshold value or more.

2. The walking condition determining device according to claim 1, wherein the measuring means comprises a second measuring means for measuring, as a second parameter, a longitudinal position of a bottom end portion of a leg with respect to a top end portion of the leg of the walker, and when the determining means determines that the walker is in the slope walking condition, the determining means determines that the walker is in an ascending walking condition if the plot in the determination space indicates an existence pattern in which the plot is located in a predetermined positive region wherein the second parameter takes a positive threshold value or more, whereas the determining means determines that the walker is in a descending walking condition if the plot indicates an existence pattern in which the plot is in a predetermined negative region wherein the second parameter takes a negative threshold value or less.

3. The walking condition determining device according to claim 1, comprising a second storage means for storing joint-to-joint distances of the legs of the walker and an angle sensor for measuring joint angles of the legs, wherein a first and a second measuring means measure first and second parameters on the basis of leg joint-to-joint distances stored by the second storage means and joint angles measured by the angle sensor.

4. The walking condition determining device according to claim 2 comprising a second storage means for storing joint-to-joint distances of the legs of the walker and an angle sensor for measuring joint angles of the legs, wherein a first and a second measuring means measure first and second parameters on the basis of leg joint-to-joint distances stored by the second storage means and joint angles measured by the angle sensor.

* * * * *

UNITED STATES PATENT AND TRADEMARK OFFICE
CERTIFICATE OF CORRECTION

PATENT NO. : 7,220,231 B2
APPLICATION NO. : 10/491853
DATED : May 22, 2007
INVENTOR(S) : Ashihara et al.

It is certified that error appears in the above-identified patent and that said Letters Patent is hereby corrected as shown below:

In the Drawings, Sheet 5 of 5, FIG. 5 (a) was omit, please replace Sheet 5 of 5 with the attached sheet that is illustrated.

Signed and Sealed this

Eleventh Day of May, 2010

David J. Kappos
*Director of the United States Patent and Trademark Office*